(12) United States Patent
Taylor

(10) Patent No.: US 8,501,426 B2
(45) Date of Patent: Aug. 6, 2013

(54) METHOD FOR IDENTIFYING PROTEASE INHIBITORS

(75) Inventor: William P. Taylor, Littleton, MA (US)

(73) Assignee: Vertex Pharmaceutical Incorporated, Cambridge, MA (US)

( * ) Notice: Subject to any disclaimer, the term of this patent is extended or adjusted under 35 U.S.C. 154(b) by 0 days.

(21) Appl. No.: 13/294,635

(22) Filed: Nov. 11, 2011

(65) Prior Publication Data
US 2012/0058502 A1    Mar. 8, 2012

Related U.S. Application Data

(63) Continuation of application No. 12/380,323, filed on Feb. 26, 2009, now abandoned, which is a continuation of application No. PCT/US2007/018945, filed on Aug. 28, 2007.

(60) Provisional application No. 60/840,573, filed on Aug. 28, 2006.

(51) Int. Cl.
C12Q 1/34        (2006.01)
C12Q 1/37        (2006.01)
C12Q 1/44        (2006.01)
C12Q 1/70        (2006.01)
G01N 33/53       (2006.01)

(52) U.S. Cl.
USPC ............. 435/7.6; 435/23; 435/5; 435/7.72; 435/18; 435/19

(58) Field of Classification Search
None
See application file for complete search history.

(56) References Cited

U.S. PATENT DOCUMENTS 5,739,002 A    4/1998 De Francesco et al.
6,251,583 B1   6/2001 Zhang et al.

FOREIGN PATENT DOCUMENTS

| WF | WO2005/043118 A2 | 5/2005 |
| WO | WO 0107407 A1 * | 2/2001 |
| WO | WO2005/058821 A | 6/2005 |

OTHER PUBLICATIONS

Sali et al. Serine Protease of Hepatitis C Virus Expressed in Insect Cells as the NS3/4A Complex. Biochemistry 1998, vol. 37, p. 3392-3401.*

Landro, J. A., et al., Mechanistic Role of an NS4A Peptide Cofactor with the Truncated NS3 Protease of Hepatitis C Virus: Elucidation of the NS4A Stimulatory Effect via Kinetic Analysis and Inhibitor Mapping, Biochemistry, 1997, pp. 9340-9348, vol. 36, No. 31, American Chemical Society.

Johansson, A., et al., Inhibition of Hepatitis C Virus NS3 Protease Activity by Product-Based Peptides is Dependent on Helicase Domain, Bioorganic & Medicinal Chemistry Letters 11, 2001, pp. 203-206, Elsevier Science Ltd.

* cited by examiner

*Primary Examiner* — Louise Humphrey

(74) *Attorney, Agent, or Firm* — Honigman Miller Schwartz and Cohn LLP; Noel E. Day; Jonathan P. O'Brien

(57) ABSTRACT

The invention describes a method for assaying HCV NS3 protease activity using an NS3•4A protease molecule. The invention also provides a method for screening and identifying modulators of NS3 protease.

19 Claims, No Drawings

METHOD FOR IDENTIFYING PROTEASE INHIBITORS

This application is a continuation of U.S. Nonprovisional application Ser. No. 12/380,323, filed on Feb. 26, 2009, which is a continuation of PCT Application No. PCT/US2007/018945 filed on Aug. 28, 2007, which claims priority to U.S. Provisional Application No. 60/840,573, filed on Aug. 28, 2006, the contents of which are incorporated herein by reference in their entireties.

FIELD OF THE INVENTION

The invention relates to methods for assaying the activity of Hepatitis C NS3 protease and for methods of screening for inhibitors of HCV NS3 protease.

BACKGROUND

Infection by hepatitis C virus (HCV) is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31, (Suppl. 1), pp. 17-24 (1999)]. Nearly four million individuals may be infected in the United States alone [M. J. Alter et al., "The Epidemiology of Viral Hepatitis in the United States, Gastroenterol. Clin. North Am., 23, pp. 437-455 (1994); M. J. Alter "Hepatitis C Virus Infection in the United States," J. Hepatology, 31, (Suppl. 1), pp. 88-91 (1999)].

The HCV genome encodes a polyprotein of 3010-3033 amino acids, which has the structure $NH_2$-C-E1-E2-p7-NS2-NS3-NS4A-NS4B-NS5A-NS5B-COOH [Q. L. Choo, et. al., "Genetic Organization and Diversity of the Hepatitis C Virus," Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)]. The NS3 protein also possesses helicase and NTPase domains.

The HCV NS3 serine protease and its associated cofactor, NS4A, help process all of the viral enzymes, and are thus considered essential for viral replication. This processing appears to be analogous to that carried out by the human immunodeficiency virus aspartyl protease, which is also involved in viral enzyme processing. HIV protease inhibitors inhibit viral protein processing and are potent antiviral agents in humans, indicating that interrupting this stage of the viral life cycle results in therapeutically active agents. Consequently the analogous HCV NS3 protease and NS4A are attractive targets for drug discovery.

Several potential HCV protease inhibitors have been described [PCT Publication Nos. WO 02/18369, WO 02/08244, WO 00/09558, WO 00/09543, WO 99/64442, WO 99/07733, WO 99/07734, WO 99/50230, WO 98/46630, WO 98/17679 and WO 97/43310; U.S. Pat. No. 5,990,276; M. Llinas-Brunet et al., Bioorg. Med. Chem. Lett., 8, pp. 1713-18 (1998); W. Han et al., Bioorg. Med. Chem. Lett., 10, 711-13 (2000); R. Dunsdon et al., Bioorg. Med. Chem. Lett., 10, pp. 1571-79 (2000); M. Llinas-Brunet et al., Bioorg. Med. Chem. Lett., 10, pp. 2267-70 (2000); and S. LaPlante et al., Bioorg. Med. Chem. Lett., 10, pp. 2271-74 (2000)]. Nevertheless, the current understanding of HCV has not led to any other satisfactory anti-HCV agents or treatments. The only established therapy for HCV disease is interferon treatment. However, interferons have significant side effects [M. A. Wlaker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only about 25% of cases [O. Weiland, "Interferon Therapy in Chronic Hepatitis C Virus Infection", FEMS Microbiol. Rev., 14, pp. 279-288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents. Consequently, an assay that can identify more effective HCV NS3 protease inhibitors is needed.

SUMMARY

The present invention provides a method for assaying HCV NS3 protease activity using an NS3•4A protease molecule. The invention also provides a method for screening and identifying modulators of NS3 protease.

In a first aspect, the invention provides a method for measuring the activity of HCV NS3 protease by adding to a sample containing an isolated protein comprising SEQ ID NO:1 and a peptide substrate based on the NS5A/5B cleavage site for HCV genotype 1a. The substrate and products are separated by HPLC and the product peaks are quantitated. In an embodiment of the first aspect, the method further comprises adding to the sample an NS4A cofactor peptide comprising SEQ ID NO:4. In another embodiment, the peptide substrate can comprise the sequence of SEQ ID NO:2, SEQ ID NO:5 or SEQ ID NO:6.

In yet another embodiment, the substrate comprises SEQ ID NO:2 and the product peak is quantitated using absorbance data collected at 210 ηm. The C-terminal product peak can also be quantified using fluorescence data collected at about 350 ηm excitation/about 490 ηm emission when the substrate comprises SEQ ID NO:5. If the substrate is SEQ ID NO:6, the N-terminal product peak can be quantitated using fluorescent data collected at about 440 ηm excitation/about 520 ηm emission.

In another aspect, the invention provides a method for identifying modulators of the Hepatitis C NS3•4A protease. In this method, a test compound is added to a sample that includes a protein comprising SEQ ID NO:1. A peptide substrate based on the NS5A/NS5B cleavage site for Hepatitis C genotype 1a is added and the substrate and products are separated using HPLC and the product peaks are quantitated. In one embodiment, the method further comprises adding to the sample an NS4A cofactor peptide comprising SEQ ID NO:4.

In yet another aspect, the invention provides a method for determining whether a test compound modifies the activity of the NS3 protease or the activity of the NS4A cofactor. In this method, a test compound added to a sample that includes a protein comprising SEQ ID NO:1. An NS4A cofactor peptide is added and a peptide substrate based on the NS5A/NS5B cleavage site for Hepatitis C genotype 1a is also added. First amounts of products are measured by separating the substrate and products on a reverse phase HPLC column; and quantifying the product peaks. First amounts of products are compared to second amounts of products, wherein the second amounts of products are measured in the absence of a NS4A cofactor peptide. In one embodiment, the NS4A cofactor peptide comprises SEQ ID NO:4. In another embodiment, the peptide substrate is SEQ ID NO:2, SEQ ID NO:5 or SEQ ID NO:6.

In still yet another aspect, the invention provides a kit comprising a sample that includes a protein containing SEQ ID NO:1 and a peptide substrate based on the NS5A/NS5B cleavage site for Hepatitis C genotype 1a. In one embodiment, the kit further comprises an NS4A cofactor peptide comprising SEQ ID NO:4. In another embodiment the peptide substrate is SEQ ID NO:2, SEQ ID NO:5 or SEQ ID NO:6, or a combination thereof. In yet other embodiments the kit further comprises one or more known modulators of NS4A cofactor and one or modulators of NS3 protease.

Sequences

SEQ ID NO:1 NS3•4A protein sequence with an N-terminal histidine tag
SEQ ID NO:2 NS5AB substrate
SEQ ID NO:3 NS4A, KK4A cofactor peptide
SEQ ID NO:4 NS4A cofactor peptide
SEQ ID NO:5 NS5AB-EDANS substrate
SEQ ID NO:6 FITC-NS5AB-1 substrate Definitions As used herein, "analog" refers to derivatives of the reference molecule, such as substrates or cofactors, which retain desired activity, such as ability to be cleaved by the NS3 protease or to act as a cofactor for the protease. In general, the term "analog" refers to compounds having a native peptide sequence and structure with one or more amino acid additions, substitutions and/or deletions. The amino acid changes include non-naturally occurring amino acids.

For polypeptides and proteins, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. The polypeptide of interest, for instance, may include up to about 5-10 conservative or non-conservative amino acid substitutions, or even up to about 15-25 conservative or non-conservative amino acid substitutions, or any integer between 5 and 25, so long as the desired function of the molecule remains intact. One of skill in the art may readily determine regions of the molecule of interest that can tolerate change by reference to Hopp/Woods and Kyte-Doolittle plots, well known in the art.

By "isolated" is meant, when referring to a polypeptide, that the indicated molecule is separate and discrete from the whole organism with which the molecule is found in nature or is present in the substantial absence of other biological macro-molecules of the same type.

As used in connection with the present invention, the term "polypeptide" or "protein" refers to a polymer in which the monomers are amino acid residues which are joined together through amide bonds. When the amino acids are alpha-amino acids, either the L-optical isomer or the D-optical isomer can be used. The term "polypeptide" as used herein is intended to encompass any amino acid sequence and includes modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein. "Substantially the same" or "substantially similar" means that an amino acid sequence is largely, but not entirely, the same, but retains a functional activity of the sequence to which it is related. In general, two amino acid sequences are "substantially the same" or "substantially homologous" if they are at least 85% identical.

Abbreviations

EDANS 5-[(2'-aminoethyl)amino]napthalenesulfonic acid
Abu aminobutyric acid
DTT dithiothreitol
DMF N,N-dimethylformamide
NS3 Hepatitis C non-structural protein 3
NS4A Hepatitis C non-structural protein 4A

DETAILED DESCRIPTION

I. Protease Assay and Identification of Protease Modulators

The method of the present invention identifies modulators of the Hepatitis C NS3 protease and/or modulators of the NS3•4A protease and cofactor by measuring the activity of the Hepatitis C NS3 protease in vitro. The method includes (a) providing a sample that includes an isolated protein with NS3 protease activity, (b) adding a peptide substrate, (c) optionally adding an NS4A cofactor peptide, (d) separating the substrate and products, and quantifying the product peaks. The method can be used to detect modulators of NS3 protease and/or NS3•4A protease and its cofactor, including activators and inhibitors.

A. NS3 Protease Protein

The protease protein can comprise the entire NS3 polypeptide of HCV, the NS3 and NS4A polypeptide, and longer polypeptides that include NS3, NS4A and NS4B. Shorter protease polypeptides can also be used in the assay, including, for example, the NS3 polypeptide and a fragment comprising from 1 to 53 amino acids of the NS4A polypeptide. The protease protein can also comprise shorter polypeptides that have protease activity, for example, the first 181 amino acids of the NS3 protein or longer fragments of the NS3 protein. The NS3-4A polypeptides and the NS3-4A-4B polypeptides can be continuous as in the HCV polyprotein, or the NS3 and NS4A polypeptides can be interrupted by a linker or other peptide sequence. Likewise, the NS3 and NS4A-4B polypeptides can be continuous or interrupted. The cleavage site between NS3 and NS4A can be mutated in the nucleic acid sequence, before it is expressed, so that upon expression, NS4A remains covalently bound to NS3.

The protease proteins can be fusion proteins containing a heterologous protein attached. For example, an N- or C-terminal histidine or GST tag can be added to the protease proteins to aid in purification. Other peptides or components can also be added, for example to immobilize the protease protein on a solid support.

Polynucleic acids encoding the protease proteins can inserted into expression vectors using recombinant DNA techniques and expressed in a number of cells or organisms including, without limitation, bacteria, such as *E. coli*; yeast, such as *Saccharomyces cerevisiae*, other yeasts and fungi, insect cells using a baculovirus vector or other expression system and mammalian systems, including cultured cells. The vectors and expression systems for the above are well known to those skilled in the art and can be found in *Current Protocols in Molecular Biology*, Vol. 2, Ed. Ausubel, et al., Greene Publish. Assoc. & Wiley Interscience, 1988; with supplements 2007, which is incorporated herein by reference.

B. Substrate

The substrate can be a peptide or a modified peptide that mimics one of the natural cleavage sites of the NS3 protease, sequences of HCV protease sites NS5A/5B, NS4A/4B and NS4B/5A (Grakoui et al., Virology, 67:2832-43, 1993). The substrate comprises a recognition site flanked on both sides by at least 3 amino acids, which can be those amino acids naturally adjacent to the protease cleavable peptide bond. The substrate peptides can be as short as 8 amino acids or can be longer than 20 amino acids. One or more copies of a protease recognition site can be present in the substrate peptide, and they can be present in series. Depsipeptide substrates, peptides with at least one ester bond in the peptide, can also be used. Other residues, such as non-naturally occurring amino acids can be added or substituted for amino acids in the peptide substrate. The substrate peptides can also contain modifications, including for example, rare amino acids and dextra-amino acids. The modified peptides can be chemically synthesized.

The substrate polypeptide can be used without a signal used to detect cleavage of the substrate (detectable signal), for example, the NS5AB peptide of SEQ ID NO:2. The substrate can also have a fluorescent label, such as EDANS (1-naphthalenesulfonic acid-5(2-aminoethylamide), as in the NS5AB-EDANS peptide of SEQ ID NO:5, FITC (fluorescein isothiocyanate), as in FITC-NS5AB-1 of SEQ ID NO:6, or other fluorescent labels. The label can be attached to the N-terminal or C-terminal end of the substrate, or can be attached to an internal residue. Other fluorescent labels known to the skilled artisan can also be used.

The substrate can also be labeled with a chromogenic substrate that can be detected upon cleavage. For example, the C-terminal carboxyl groups can be esterified with a chromophoric alcohol, including 3- or 4-nitrophenol, 7-hydroxy-4-methyl-coumarin and 4-phenylazophenol, as described in Zhang et al., Analytical Biochemistry, 270:268-75, 1999. The cleaved substrate is detected spectrophotometrically. For example, 3-nitrophenol and 7-hydroxy-4-methyl-coumarin can be detected at 340 ηm, 4-phenylazophenol at 370 ηm, and 4-nitrophenol at 400 ηm. Other chromogenic substrates can also be used.

The substrate can also labeled with two labels that form a Resonance Energy Transfer (RET) pair. For example, the substrate can contain a chromophore and a fluorophore placed on opposites of the scissile bond so that the chromophore quenches the fluorescence of the fluorophore. Upon substrate cleavage, the chromophore and the fluorophore are separated and fluorescence can be detected. For example, EDANS can be on one side of the scissile bond and a DABCYL (4-dimethylaminophenylazobenzoyl) group attached to an amino acid residue on the other side. DABCYL must be close enough to quench the fluorescence of EDANS, for example, DABCYL and EDANS can be separated by approximately six residues or more. An NS3 protease assay using a substrate containing a RET pair is described in the PCT publication WO 05/043118, which is incorporated herein by reference. DABCYL can also be used to quench the fluorescence of MCA (methoxycoumarin acetic acid), TET (tetrachlorofluorescein), JOE (carboxy-4'-5'-dichloro-2',7'-dimethoxyfluorescein) FAM (carboxyfluorescein) and other fluorophores and chromophores.

A detectable signal on the substrate can also comprise an epitope, an antibody binding region, an enzyme, a protein binding domain or a nucleic acid binding domain. The substrate can also contain a radioactive label.

The substrate can be attached to a solid support. For example, the substrate can be attached to a solid support coated with antibodies that recognize an epitope on the N- or C-terminal end of the peptide substrate. In one embodiment, a FLAG tag can be attached to the N-terminal part of the substrate and attached to a microtiter plate whose wells have been coated with anti-FLAG antibodies. The solid support can also be latex particles, paramagnetic particles, paramagnetic latex particles, membranes, polystyrene microbeads and glass beads. The substrate can also be attached to a gel chromatography matrix, such as affigel, via crosslinking. A substrate attached to a solid support can be labelled as described above.

C. NS4A Cofactor

An NS4A cofactor can be added to the assay to increase the activity of the NS3 protease. The cofactor can be added to any of the NS3 protease polypeptides described above, including those that include the NS4A polypeptide, e.g., SEQ ID NO:1. The cofactor can be the entire 54 amino acid NS4A peptide or can be shorter versions of it. If shorter versions are used, the NS4A cofactor includes the central part of NS4A, amino acids 21-34 of NSA4. For example, the cofactor can be the peptide with SEQ ID NO:4, which is 23 amino acids long and includes the central part of NSA4. The cofactor can also consist of amino acids 21-34 of NSA4. Longer peptides from 14 amino acids up to the entire 54 amino acids of the NS4A peptide can also be used.

D. Separation and Quantitation of the Products.

Quantification of the reaction products depends on the substrate used. For a substrate without a label, such as NS5AB [SEQ ID NO:2], the products can be separated by chromatography, usually HPLC, and the product peaks quantified. For substrates with a fluorescent label, such as EDANS and FITC, the products can also be separated by chromatography, such as HPLC, and the product peaks quantified.

If a chromogenic substrate is used, such as a peptide substrate labelled with 3-nitrophenol, the reaction product can be detected spectrophotometrically, as stated above.

If a peptide substrate is labelled with a RET pair, the reaction product can be detected by fluorescence using appropriate excitation and emission wavelengths.

E. Modulators

The invention provides a method for identifying a compound which modulates NS3 protease activity including incubating components comprising the test compound and the polypeptide containing NS3 protease, under conditions sufficient to allow the components to interact and determining the affect of the compound on the activity of the protease. The term "affect" as used herein, encompasses any means by which NS3 protease activity can be modulated. Such compounds include, for example, polypeptides, peptidomimetics, chemical compounds and biologic agents as described below.

Incubating includes conditions that allow contact between the test compound and NS3 protease. Contacting includes in solution and in solid phase. In one embodiment, the test ligand(s)/compound(s) can be a combinatorial library for screening a plurality of compounds. Compounds identified in the method of the invention can be further evaluated.

Hence, the method of the invention includes combinatorial chemistry methods for identifying chemical compounds that affect NS3 protease activity. Using the methods of the present invention, one can identify molecules and compounds that modulate, activate or inhibit the activity of NS3 protease.

Because the NS4A protein can also be included in the assay, the assay can also identify compounds that modulate the function of NS4A as a cofactor for NS3 protease. In this method the assay is carried out in the presence and absence of an NS4A cofactor, the products are quantified and the amounts of products are compared. By comparing the products of the following assays: (1) with NS3A protease, without NS4A cofactor and without test compound, (2) with NS3A protease, with NS4A cofactor and without test compound, (3) with NS3A protease, without NS4A cofactor and without test compound, and (4) with NS3A protease, with NS4A cofactor and with test compound, one can determine whether the test compound modulates NS3A protease, NS4A cofactor, or a combination.

A wide variety of assays can be used to screen for molecules and compounds that modulate NS3 protease activity, including labeled in vitro protein-protein binding assays, in vitro and in vivo assays that measure NS3 protease activity. Generally, a plurality of assay mixtures are run in parallel with different candidate molecule or compound concentrations to obtain a differential response to the various concentrations. Typically, one of these concentrations serves as a negative control, i.e. at zero concentration or below the level of detection.

Candidate compounds and molecules encompass numerous chemical classes, including organic molecules, such as small organic compounds having a molecular weight of more than 50 and less than about 2,500 Daltons. Candidate compounds and molecules can comprise functional groups necessary for structural interaction with proteins, particularly hydrogen bonding, and in one embodiment include at least an amine, carbonyl, hydroxyl or carboxyl group. In another embodiment, at least two of the functional chemical groups are included in the candidate compound. In yet another embodiment, the candidate molecules and compounds comprise cyclical carbon or heterocyclic structures and/or aromatic or polyaromatic structures substituted with one or more of the above functional groups. Candidate molecules and compounds are also found among biomolecules including, but not limited to peptides, saccharides, fatty acids, steroids, purines, pyrimidines, derivatives, structural analogs or combinations thereof. Candidate molecules and compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and can be used to produce combinatorial libraries. Known pharmacological agents can be subjected to directed or random chemical modifications, such as acylation, alkylation, esterification and amidification to produce structural analogs.

A variety of other reagents can be included in the screening assay. These include reagents like salts, neutral proteins, e.g., albumin, detergents, etc. that are used to facilitate optimal protein-protein binding and/or reduce non-specific or background interactions. Reagents that improve the efficiency of the assay, such as protease inhibitors, nuclease inhibitors and anti-microbial agents may be used. The mixtures of components are added in any order that provides for the requisite binding. Incubations are performed at any suitable temperature, typically between 4° C. and 40° C. Incubation periods are selected for optimum activity, but may also be optimized to facilitate rapid high-throughput screening. The details of some assay conditions are included in the examples below.

II. Kits for Detection of Protease Activity and Identification of Modulators

The materials for use in the method of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a sample containing NS3 protease polypeptide. A second container may comprise a peptide substrate for NS3 protease. The constituents may be present in liquid or lyophilized form, as desired. A third container means may comprise an NS4A cofactor peptide. A kit can also comprise a fourth and fifth container means comprising a known compound that inhibits NS3 protease and a second compound that activates NS3 protease, respectively. The kit can also comprise a sixth and seventh container means comprising a known compound that inhibits NS4A cofactor and a second compound that activates NS4A cofactor, respectively.

EXAMPLES

Example 1

Construction and Expression of the HCV NS3 Serine Protease Domain

A DNA fragment encoding residues $Ala^1$-$Ser^{181}$ of the HCV NS3 protease (GenBank CAB46913) was obtained by PCR from the HCV Con1 replicon plasmid, I$_{377}$neo/NS3-3'/wt (re-named as pBR322-HCV-Neo in this study) [V. Lohmann et al., Science, 285, pp. 110-113 (1999)] and inserted into pBEV11 (S. Chamber, et al., personal communication) for expression of the HCV proteins with a C-terminal hexa-histidine tag in *E. coli*. All constructs were confirmed by sequencing.

The expression construct for the HCV NS3 serine protease domain was transformed into BL21/DE3 pLysS *E. coli* cells (Stratagene). Freshly transformed cells were grown at 37° C. in a BHI medium (Difco Laboratories) supplemented with 100 μg/ml carbenicillin and 35 μg/mL chloramphenicol to an optical density of 0.75 at 600 ηm. Induction with 1 mM IPTG was performed for four hours at 24° C. The cell paste was harvested by centrifugation and flash frozen at −80° C. prior to protein purification. All purification steps were performed at 4° C. Next, 100 g of cell paste was lysed in 1.5 L of buffer A (50 mM HEPES (pH 8.0), 300 mM NaCl, 0.1% n-octyl-β-D-glucopyranoside, 5 mM β-mercaptoethanol, 10% (v/v) glycerol) and stirred for 30 minutes. The lysate was homogenized using a Microfluidizer (Microfluidics, Newton, Mass.), followed by ultra-centrifugation at 54,000×g for 45 minutes. Imidazole was added to the supernatant to a final concentration of 5 mM along with 2 mL of Ni-NTA resin pre-equilibrated with buffer A containing 5 mM imidazole. The mixture was rocked for three hours and washed with 20 column volumes of buffer A plus 5 mM imidazole. The HCV NS3 protein was eluted in buffer A containing 300 mM imidazole. The eluate was concentrated and loaded onto a Hi-Load 16/60 Superdex 200 column, pre-equilibrated with buffer A. The appropriate fractions of the purified HCV protein were pooled and stored at −80° C.

Example 2

HCV NS3 Protease Domain Peptide Cleavage Assay

This assay is a modification of that described by Landro, et al. (Landro J A, Raybuck S A, Luong Y C, O'Malley E T, Harbeson S L, Morgenstern K A, Rao G and Livingston D L. Biochemistry 1997, 36, 9340-9348), and uses a peptide substrate (NS5AB), based on the NS5A/NS5B cleavage site for genotype 1a HCV. The substrate stock solution (25 mM) was prepared in DMSO containing 0.2 M DTT and stored at −20° C. A synthetic peptide cofactor (KK4A) was used as a substitute for the central core region of NS4A. Peptide sequences are shown in Table 1. The reaction was performed in a 96-well microtiter plate format using 25 ηM to 50 ηM HCV NS3 protease domain in buffer containing 50 mM HEPES pH 7.8, 100 mM NaCl, 20% glycerol, 5 mM DTT and 25 μM KK4A. The final DMSO concentration was no greater than 2% v/v. Reactions were quenched by addition of trifluoroacetic acid (TFA) to yield a final concentration of 2.5%.

TABLE 1

Peptide Sequences Used with HCV NS3 Protease Domain

| Peptide | Sequence |
|---------|----------|
| NS5AB | NH$_2$-EDVV-(alpha)Abu-CSMSY-COOH [SEQ ID NO: 2] |
| KK4A | NH$_2$-KKGSVVIVGRIVLSGK-COOH [SEQ ID NO: 3] |

The SMSY product was separated from substrate and KK4A using a microbore separation method. The instrument used was a Agilent 1100 with a G1322A degasser, either a G1312A binary pump or a G1311A quaternary pump, a G1313A autosampler, a G1316A column thermostated chamber and a G1315A diode array detector. The column was a Phenomenex Jupiter, 5 μm C18, 300 Å, 150×2 mm, P/O 00F-4053-B0, with a flow-rate of 0.2 mL/min. The column thermostat was at 40° C. Mobile phases were HPLC grade H$_2$O/0.1% TFA (solvent A) and HPLC grade CH$_3$CN/0.1% TFA (solvent B). The SMSY product peak was quantified using the data collected at 210 ηM.

Example 3

Construction and Expression of NS3•4A Protease

Using standard recombinant DNA techniques, a cDNA fragment encoding the peptide sequence for NS3 and NS4A, residues Ala$_{1027}$ to Cys$_{1711}$ from the HCV sub-type strain 1a, containing an N-terminal hexa-histidine sequence, was cloned into the baculoviral transfer vector pVL1392 (Webb N R and Summers M D (1990) Expression of proteins using recombinant baculoviruses, Techniques 2:173-188). Recombinant baculovirus containing NS3•4A was produced by co-transfection of pVL1392-His-NS3•4A with linearized *Autographa californica* nuclear polyhedrosis virus (AcMNPV) DNA into *Spodoptera frugoperda* (Sf9) insect cells. The transfected insect cells containing recombinant baculovirus clones were subsequently isolated by plaque purification. High-titer clonal baculovirus was routinely used to infect Sf9 insect cells for protein production. In production, Sf9 cells were grown at 27° C. until they reached a density of 2.0×10$^6$ cells/mL. At this point, the insect cells were infected with virus. After 72 hours or when the cell viability was between 70-80% the culture was harvested and the cells were ready for purification.

Example 4

Purification of NS3•4A Protein

The NS3•4A protein (SEQ ID NO:1) was purified as follows. Cell paste was thawed in at least five volumes of Lysis Buffer (50 mM Na$_2$HPO$_4$ pH 8.0, 10% Glycerol, 300 mM NaCl, 5 mM β-mercaptoethanol, 0.2 mM PMSF, 2.5 μg/mL Leupeptin, 1.0 μg/mL E64, 2.0 μg/mL Pepstatin) per gram of cell paste. The cell paste was then homogenized on ice using a Dounce homogenizer. The cells were mechanically disrupted by passing once through a microfluidizer (Microfluidics Corporation, Newton, Mass.), and the cell lysate was collected on ice. The cell lysate was centrifuged at 100,000×g for 30 minutes at 4° C. and the supernatants were decanted. Optionally, the pellet was resuspended in wash buffer (Lysis Buffer+0.1% (β-octyl glucopyranoside), homogenized using a Dounce homogenizer and centrifuged at 100,000×g for 30 minutes at 4° C. Insoluble NS3•4A was extracted from the pellets by resuspending in Extraction Buffer (Lysis Buffer+0.5% lauryl maltoside) using 2.5 mL/g cell paste. The mixture was homogenized using a Dounce homogenizer and mixed at 4° C. for three hours or more. The mixture was centrifuged at 100,000×g for 30 minutes at 4° C. The supernatants were decanted and pooled.

The NS3•4A protein was further purified using Nickel-NTA metal affinity chromatography. Imidazole from a 2 M stock, pH 8.0, solution was added to the pooled supernatants so that the final concentration of imidazole was 10 mM. The supernatants were incubated batchwise overnight at 4° C. with Nickel-NTA affinity resin that had been pre-equilibrated with Lysis Buffer+10 mM imidazole. 1 mL of resin per 5 µg of expected NS3-4A was used. The resin was next settled by gravity or by centrifugation at 500×g for five minutes. The resin was poured into a gravity flow column and washed with 10 or more column volumes of Nickel Wash Buffer (Lysis Buffer+0.1% lauryl maltoside+10 mM imidazole). The column was eluted with three to four column volumes of Nickel Elution Buffer (Nickel Wash Buffer+300 mM imidazole). The elution fractions were collected on ice and evaluated using SDS-PAGE. To prevent NS3•4A proteolysis, 100 µM DFP protease inhibitor was added to gel samples before adding SDS sample buffer and boiling. The peak fractions were pooled and protein concentration was determined by measuring absorbance at 280 ηm and by dividing by the extinction coefficient (e), which for NS3•4A is 1.01.

The NS3•4A protein was purified further using gel filtration chromatography. A Superdex 200 26/60 column was equilibrated with Superdex Buffer (20 mM HEPES pH 8.0, 10% glycerol, 300 mM NaCl, 10 mM β-mercaptoethanol, 0.05% lauryl maltoside) at a rate of 3 mL/min. The nickel purified NS3•4A was concentrated in a Centriprep 30 to greater than 2 mg/mL, if necessary, and was filtered through a 0.2 µm syringe filter and up to 10 mL was loaded onto the Superdex 200 column. After 0.3 column volumes passed through, 4-5 mL fractions were collected. Fractions were evaluated by SDS-PAGE. NS3•4A protein elutes in two peaks. Peak 1 contains aggregated NS3•4A and peak 2 contains active protein. The fractions of peak 2 were pooled, aliquoted and frozen at −70° C.

TABLE 2

Analysis of NS3•4A Protein

| ANALYSIS | ENTIRE PROTEIN |
|---|---|
| Length | 695 amino acids |
| Molecular Weight | 74,347.78 |
| 1 microgram | 13.450 pico moles |
| Molar Extinction Coefficient | 73430 |
| 1 $A_{280}$ corresponds to | 1.01 mg/mL |
| Isoelectric Point | 6.50 |
| Charge at pH 7 | −3.58 |

Example 5

HCV NS3 Peptide Cleavage Assay

This assay follows the cleavage of a peptide substrate by full-length hepatitis C viral protein NS3•4A. One of three peptide substrates based on the NS5A/NS5B cleavage site for genotype 1a HCV, shown in table 3 below, is used to measure enzyme activity. All substrate stock solutions (25 mM) were prepared in DMSO containing 0.2 M DTT and stored at −20° C. A synthetic peptide cofactor (NS4A Peptide) was used to supplement NS4A. Peptide sequences are shown in Table 3. The hydrolysis reaction was performed in a 96-well microtiter plate format using 100 ηM to 125 ηM HCV NS3•4A in buffer containing 50 mM HEPES pH 7.8, 100 mM NaCl, 20% glycerol, 5 mM DTT and 25 µM NS4A peptide. The final DMSO concentration was no greater than 2% v/v. Reactions using NS5AB or NS5AB-EDANS as substrate were quenched by the addition of 10% trifluoroacetic acid (TFA) to yield a final TFA concentration of 2.5%. Reactions using FITC-NS5AB-1 as substrate were quenched by the addition of 0.4 M formic acid to yield a final concentration of 0.08 M acid.

Enzymatic activity was assessed by separation of substrate and products using reverse phase HPLC. The instrument used was an Agilent 1100 with a G1322A degasser, either a G1312A binary pump or a G1311A quaternary pump, a G1313A autosampler, a G1316A column thermostated chamber, a G1321A fluorescence detector and a G1315A diode array detector. The column thermostat was at 40° C. For substrate NS5AB, the column was a Phenomenex Jupiter, 5 µm C18, 300 Å, 150×2 mm, P/O 00F-4053-B0, with a flow-rate of 0.2 mL/min using HPLC grade $H_2O$/0.1% TFA (solvent A) and HPLC grade $CH_3CN$/0.1% TFA (solvent B) as mobile phases. The C-terminal product peak ($NH_2$-SMSY-COOH) was quantified using the absorbance data collected at 210 ηm. For substrate NS5AB-EDANS the column was a Phenomenex Aqua, 5 µm C18, 125 Å, 50×4.6 mm, P/O 00B-4299-E0, with a flow-rate of 1.0 mL/min using HPLC grade $H_2O$/0.1% TFA (solvent A) and HPLC grade $CH_3CN$/0.1% TFA (solvent B) as mobile phases. The C-terminal product peak ($NH_2$-SMSYT-Asp(EDANS)-KKK-COOH) was quantified using the fluorescence data collected at 350 ηm excitation/490 ηm emission. For substrate FITC-NS5AB-1 the column was a Phenomenex Prodigy, 5 µm ODS(2), 125 Å, 50×4.6 mm, P/O 00B-3300-E0, with a flow-rate of 1.0 mL/min using 10 mM sodium phosphate pH 7.0 in HPLC grade $H_2O$ (solvent A) and 65% HPLC Grade $CH_3CN$/35% 10 mM sodium phosphate pH 7.0 in HPLC grade $H_2O$ (solvent B) as mobile phases. The N-terminal product peak (FITC-Ahx-EDVV-(alpha)Abu-C-COOH) was quantified using the fluorescence data collected at 440 ηm excitation/520 ηm emission. Alternatively, the ratio of N-terminal product to unreacted FITC-NS5AB-1 substrate was determined using a Caliper LabChip 3000 with detection at 488 ηm excitation/530 ηm emission, using a chip buffer of 100 mM Tris pH 7.0, 10 mM EDTA, 0.01% (v/v) Brij-35, and 0.1% (v/v) CR-3.

TABLE 3

Peptide Sequences Used with HCV NS3

| Peptide | Sequence |
|---|---|
| NS4A Peptide | $NH_2$-KKGSVVIVGRIVLSGKPAIIPKK-COOH [SEQ ID NO: 4] |
| NS5AB | $NH_2$-EDVV-(alpha)Abu-CSMSY-COOH [SEQ ID NO: 2] |
| NS5AB-EDANS | $NH_2$-EDVV-(alpha)Abu-CSMSYT-Asp(EDANS)-KKK-COOH [SEQ ID NO: 5] |
| FITC-NS5AB-1 | FITC-Ahx-EDVV-(alpha)Abu-CSMSYTKK-$NH_2$ [SEQ ID NO: 6] |

Example 6

Determination of $K_m$ and $V_{max}$

To determine the kinetic parameters $K_m$ and $V_{max}$, the HCV NS3 protease domain or HCV NS3•4A was reacted with peptide substrate under the assay conditions described above. Peptide substrate concentration was varied between 3 μM and 200 μM, with less than 20 percent conversion at all substrate concentrations. The ratio of the product peak area (as determined by reverse phase HPLC) to the reaction time yielded a rate of enzyme catalyzed hydrolysis. These rate vs. substrate concentration data points were fit to the Michaelis-Menten equation using non-linear regression. The value of $k_{cat}$ was determined from $V_{max}$ using the nominal protease concentration and a fully cleaved substrate peptide as an instrument calibration standard.

TABLE 4

Kinetic Parameters for Peptide Substrates with HCV NS3 or NS3 Protease Domain

| Enzyme | Substrate | Km (μM) | $k_{cat}$/Km (M$^{-1}$sec$^{-1}$) |
|---|---|---|---|
| NS3 Protease Domain | NS5AB | 25 | $3.0 \times 10^4$ |
| NS3•4A | NS5AB | 30 | $7.9 \times 10^3$ |
| NS3•4A | NS5AB-EDANS | 56 | $1.4 \times 10^3$ |
| NS3•4A | FITC-NS5AB-1 | 15 | $1.2 \times 10^3$ |

Example 7

Determination of Compound Potency

To evaluate apparent $K_i$ values, all components except the test compound and substrate were pre-incubated for 5 to 10 minutes at room temperature. Then, test compound, dissolved in DMSO, was added to the mixture and incubated for either 15 minutes or 60 minutes at 30° C. Neat DMSO was included as a no inhibitor control. The cleavage reaction was initiated by the addition of peptide substrate at a concentration either equal to Km or equal to one-half times $K_m$, and allowed to proceed at 30° C. for 20 minutes. At the end of the reaction the mixture was quenched, and the extent of reaction was determined as described above. Eleven concentrations of compound were used to titrate enzyme activity for inhibition. Activity vs. inhibitor concentration data points were fit to the Morrison equation describing competitive tight-binding enzyme inhibition using non-linear regression (Sculley M J and Morrison J F. Biochim. Biophys. Acta. 1986, 874, 44-53).

A number of compounds were tested in the assays described in Example 2 and Example 5 above. The compounds are described in described in PCT International Publication No. WO 07/025,307, which is incorporated herein by reference in its entirety, and the results are reported in Table 10 of the same PCT publication (PCT International Publication No. WO 07/025,307).

Other Embodiments

The foregoing examples and description are not meant to limit the invention. While the invention has been described in terms of different specific embodiments and examples, those skilled in the art will recognize that various changes and modifications can be made through routine experimentation without departing from the spirit and scope of the invention. The invention should be understood as not being limited by the foregoing detailed description, but as being defined by the appended claims and their equivalents.

All patent documents and journal articles cited above are incorporated herein by reference in their entirety.

What is claimed is:

1. A method for measuring the activity of the Hepatitis C NS3 protease comprising:
   a) providing a sample comprising an isolated protein comprising SEQ ID NO:1 and a sample comprising an NS4A cofactor peptide comprising SEQ ID NO:4;
   b) adding a peptide substrate based on the NS5A/NS5B cleavage site for Hepatitis C genotype 1a;

c) separating the substrate and products on a reverse phase HPLC column; and d) quantifying the product peaks.

2. The method of claim 1 wherein the peptide substrate is selected from the group consisting of SEQ ID NO:2, SEQ ID NO:5 and SEQ ID NO:6.

3. The method of claim 2, wherein the peptide substrate is SEQ ID NO:2.

4. The method of claim 2, wherein the peptide substrate is SEQ ID NO:5.

5. The method of claim 2, wherein the peptide substrate is SEQ ID NO:6.

6. The method of claim 3, wherein the C-terminal product peak is quantified using absorbance data collected at about 210 ηm.

7. The method of claim 4, wherein the C-terminal product peak is quantified using fluorescence data collected at about 350 ηm excitation/about 490 ηm emission.

8. The method of claim 5, wherein the N-terminal product peak is quantified using fluorescent data collected at about 440 ηm excitation/about 520 ηm emission.

9. A method for identifying modulators of the Hepatitis C NS3 protease comprising a) providing a sample comprising a protein comprising SEQ ID NO:1;

b) introducing a test compound to the sample;

c) adding a peptide substrate based on the NS5A/NS5B cleavage site for Hepatitis C genotype 1a;

d) separating the substrate and products on a reverse phase HPLC column; and e) quantifying the product peaks.

10. The method of claim 9 further comprising adding to the sample and test compound an NS4A cofactor peptide comprising SEQ ID NO:4.

11. The method of claim 9 or 10, wherein the peptide substrate is selected from the group consisting of SEQ ID NO:2, SEQ ID NO:5 and SEQ ID NO:6.

12. A method for determining whether a test compound modifies the activity of the NS3 protease or the activity of the NS4A cofactor comprising:

a) providing a sample comprising a protein comprising SEQ ID NO:1;

b) introducing a test compound to the sample;

c) adding an NS4A cofactor peptide;

d) adding a peptide substrate based on the NS5A/NS5B cleavage site for Hepatitis C genotype 1a;

e) measuring first amounts of products by separating the substrate and products on a reverse phase HPLC column; and quantifying the product peaks; and f) comparing first amounts of products to second amounts of products, wherein the second amounts of products are measured in the absence of a NS4A cofactor peptide.

13. The method of claim 12, wherein the NS4A cofactor peptide comprises SEQ ID NO:4.

14. The method of claim 12 or 13, wherein the peptide substrate is selected from the group consisting of SEQ ID NO:2, SEQ ID NO:5 and SEQ ID NO:6.

15. A kit comprising a) a sample comprising a protein containing SEQ ID NO:1 and b) a peptide substrate based on the NS5A/NS5B cleavage site for Hepatitis C genotype 1a.

16. The kit according to claim 15 further comprising an NS4A cofactor peptide comprising SEQ ID NO:4.

17. The kit according to claim 15 or 16, wherein the peptide substrate is selected from the group consisting of SEQ ID NO:2, SEQ ID NO:5 and SEQ ID NO:6, or a combination thereof.

18. The kit according to claim 17, further comprising one or more known modulators of NS3 protease.

19. The kit according to claim 18, further comprising one or more known modulators of NS4A cofactor.

* * * * *

UNITED STATES PATENT AND TRADEMARK OFFICE
CERTIFICATE OF CORRECTION

PATENT NO. : 8,501,426 B2
APPLICATION NO. : 13/294635
DATED : August 6, 2013
INVENTOR(S) : William P. Taylor Page 1 of 1

It is certified that error appears in the above-identified patent and that said Letters Patent is hereby corrected as shown below:

In the Claims

Col. 21, line 41, in claim 8 of the patent, please delete "fluorescent" and replace with "fluorescence."

Signed and Sealed this
Twenty-second Day of October, 2013

Teresa Stanek Rea
*Deputy Director of the United States Patent and Trademark Office*

SEQUENCE LISTING

```
<160> NUMBER OF SEQ ID NOS: 9

<210> SEQ ID NO 1
<211> LENGTH: 695
<212> TYPE: PRT
<213> ORGANISM: Hepatitis C virus
<220> FEATURE:
<221> NAME/KEY: MISC_FEATURE
<222> LOCATION: (1)..(10)
<223> OTHER INFORMATION: Histidine tag

<400> SEQUENCE: 1

Met Ser His His His His His His Ala Met Ala Pro Ile Thr Ala Tyr
1               5                   10                  15

Ala Gln Gln Thr Arg Gly Leu Leu Gly Cys Ile Ile Thr Ser Leu Thr
            20                  25                  30

Gly Arg Asp Lys Asn Gln Val Glu Gly Glu Val Gln Ile Val Ser Thr
        35                  40                  45

Ala Thr Gln Thr Phe Leu Ala Thr Cys Ile Asn Gly Val Cys Trp Thr
    50                  55                  60

Val Tyr His Gly Ala Gly Thr Arg Thr Ile Ala Ser Pro Lys Gly Pro
65                  70                  75                  80

Val Ile Gln Met Tyr Thr Asn Val Asp Gln Asp Leu Val Gly Trp Pro
                85                  90                  95

Ala Pro Gln Gly Ser Arg Ser Leu Thr Pro Cys Thr Cys Gly Ser Ser
```

```
                 100                 105                 110
Asp Leu Tyr Leu Val Thr Arg His Ala Asp Val Ile Pro Val Arg Arg
        115                 120                 125

Arg Gly Asp Ser Arg Gly Ser Leu Leu Ser Pro Arg Pro Ile Ser Tyr
    130                 135                 140

Leu Lys Gly Ser Ser Gly Gly Pro Leu Leu Cys Pro Ala Gly His Ala
145                 150                 155                 160

Val Gly Leu Phe Arg Ala Val Cys Thr Arg Gly Val Thr Lys Ala
        165                 170                 175

Val Asp Phe Ile Pro Val Glu Asn Leu Glu Thr Thr Met Arg Ser Pro
        180                 185                 190

Val Phe Thr Asp Asn Ser Ser Pro Pro Ala Val Pro Gln Ser Phe Gln
        195                 200                 205

Val Ala His Leu His Ala Pro Thr Gly Ser Gly Lys Ser Thr Lys Val
        210                 215                 220

Pro Ala Ala Tyr Ala Ala Gln Gly Tyr Lys Val Leu Val Leu Asn Pro
225                 230                 235                 240

Ser Val Ala Ala Thr Leu Gly Phe Gly Ala Tyr Met Ser Lys Ala His
                245                 250                 255

Gly Val Asp Pro Asn Ile Arg Thr Gly Val Arg Thr Ile Thr Thr Gly
                260                 265                 270

Ser Pro Ile Thr Tyr Ser Thr Tyr Gly Lys Phe Leu Ala Asp Gly Gly
                275                 280                 285

Cys Ser Gly Gly Ala Tyr Asp Ile Ile Ile Cys Asp Glu Cys His Ser
    290                 295                 300

Thr Asp Ala Thr Ser Ile Leu Gly Ile Gly Thr Val Leu Asp Gln Ala
305                 310                 315                 320

Glu Thr Ala Gly Ala Arg Leu Val Val Leu Ala Thr Ala Thr Pro Pro
                325                 330                 335

Gly Ser Val Thr Val Ser His Pro Asn Ile Glu Glu Val Ala Leu Ser
                340                 345                 350

Thr Thr Gly Glu Ile Pro Phe Tyr Gly Lys Ala Ile Pro Leu Glu Val
                355                 360                 365

Ile Lys Gly Gly Arg His Leu Ile Phe Cys His Ser Lys Lys Lys Cys
                370                 375                 380

Asp Glu Leu Ala Ala Lys Leu Val Ala Leu Gly Ile Asn Ala Val Ala
385                 390                 395                 400

Tyr Tyr Arg Gly Leu Asp Val Ser Val Ile Pro Thr Asn Gly Asp Val
                405                 410                 415

Val Val Val Ser Thr Asp Ala Leu Met Thr Gly Phe Thr Gly Asp Phe
                420                 425                 430

Asp Ser Val Ile Asp Cys Asn Thr Cys Val Thr Gln Thr Val Asp Phe
                435                 440                 445

Ser Leu Asp Pro Thr Phe Thr Ile Glu Thr Thr Thr Leu Pro Gln Asp
                450                 455                 460

Ala Val Ser Arg Thr Gln Arg Arg Gly Arg Thr Gly Arg Gly Lys Pro
465                 470                 475                 480

Gly Ile Tyr Arg Phe Val Ala Pro Gly Glu Arg Pro Ser Gly Met Phe
                485                 490                 495

Asp Ser Ser Val Leu Cys Glu Cys Tyr Asp Ala Gly Cys Ala Trp Tyr
                500                 505                 510

Glu Leu Met Pro Ala Glu Thr Thr Val Arg Leu Arg Ala Tyr Met Asn
                515                 520                 525
```

```
Thr Pro Gly Leu Pro Val Cys Gln Asp His Leu Glu Phe Trp Glu Gly
        530                 535                 540
Val Phe Thr Gly Leu Thr His Ile Asp Ala His Phe Leu Ser Gln Thr
545                 550                 555                 560
Lys Gln Ser Gly Glu Asn Phe Pro Tyr Leu Val Ala Tyr Gln Ala Thr
                565                 570                 575
Val Cys Ala Arg Ala Gln Ala Pro Pro Ser Trp Asp Gln Met Trp
            580                 585                 590
Lys Cys Leu Ile Arg Leu Lys Pro Thr Leu His Gly Pro Thr Pro Leu
        595                 600                 605
Leu Tyr Arg Leu Gly Ala Val Gln Asn Glu Val Thr Leu Thr His Pro
    610                 615                 620
Ile Thr Lys Tyr Ile Met Thr Cys Met Ser Ala Asp Leu Glu Val Val
625                 630                 635                 640
Thr Ser Thr Trp Val Leu Val Gly Gly Val Leu Ala Ala Leu Ala Ala
                645                 650                 655
Tyr Cys Leu Ser Thr Gly Cys Val Val Ile Val Gly Arg Ile Val Leu
            660                 665                 670
Ser Gly Lys Pro Ala Ile Ile Pro Asp Arg Glu Val Leu Tyr Gln Glu
        675                 680                 685
Phe Asp Glu Met Glu Glu Cys
    690                 695

<210> SEQ ID NO 2
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: (alpha) aminobutyric acid

<400> SEQUENCE: 2

Glu Asp Val Val Xaa Cys Ser Met Ser Tyr
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 3

Lys Lys Gly Ser Val Val Ile Val Gly Arg Ile Val Leu Ser Gly Lys
1               5                   10                  15

<210> SEQ ID NO 4
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 4

Lys Lys Gly Ser Val Val Ile Val Gly Arg Ile Val Leu Ser Gly Lys
1               5                   10                  15

Pro Ala Ile Ile Pro Lys Lys
            20
```

-continued

```
<210> SEQ ID NO 5
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: (alpha) aminobutyric acid
<220> FEATURE:
<221> NAME/KEY: MOD_RES
<222> LOCATION: (12)..(12)
<223> OTHER INFORMATION: Asp (EDANS)

<400> SEQUENCE: 5

Glu Asp Val Val Xaa Cys Ser Met Ser Tyr Thr Asp Lys Lys Lys
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: FITC-2 - aminohexanoic acid
<220> FEATURE:
<221> NAME/KEY: MOD_RES
<222> LOCATION: (6)..(6)
<223> OTHER INFORMATION: (alpha) aminobutyric acid

<400> SEQUENCE: 6

Xaa Glu Asp Val Val Xaa Cys Ser Met Ser Tyr Thr Lys Lys
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 7

Ser Met Ser Tyr
1

<210> SEQ ID NO 8
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (6)..(6)
<223> OTHER INFORMATION: Asp (EDANS)

<400> SEQUENCE: 8

Ser Met Ser Tyr Thr Asp Lys Lys Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
```

-continued

```
<222> LOCATION: (1)..(1)
<223> OTHER INFORMATION: FITC-2 - aminohexanoic acid
<220> FEATURE:
<221> NAME/KEY: MOD_RES
<222> LOCATION: (6)..(6)
<223> OTHER INFORMATION: (alpha) aminobutyric acid

<400> SEQUENCE: 9

Xaa Glu Asp Val Val Xaa Cys
1               5
```